United States Patent [19]
Carney et al.

[11] Patent Number: 5,578,617
[45] Date of Patent: Nov. 26, 1996

[54] METHOD AND COMPOSITIONS FOR TREATING AGE RELATED DISORDERS

[75] Inventors: John M. Carney, Lexington, Ky.; Robert A. Floyd, Oklahoma City, Okla.

[73] Assignees: Oklahoma Medical Research Foundation, Oklahoma City, Okla.; University of Kentucky Research Foundation, Lexington, Ky.

[21] Appl. No.: 365,548

[22] Filed: Dec. 28, 1994

Related U.S. Application Data

[62] Division of Ser. No. 27,559, Mar. 5, 1993, Pat. No. 5,405,874, which is a continuation of Ser. No. 589,177, Sep. 27, 1990, abandoned, which is a continuation-in-part of Ser. No. 422,651, Oct. 17, 1989, Pat. No. 5,025,032.

[51] Int. Cl.$^6$ ............................ A61K 31/44; A61K 31/40
[52] U.S. Cl. ............................................ 514/345; 514/424
[58] Field of Search ...................................... 514/424, 345

[56] References Cited

U.S. PATENT DOCUMENTS

| | | | |
|---|---|---|---|
| 3,296,145 | 1/1967 | Findlam et al. | 514/311 |
| 3,849,934 | 11/1974 | Dorschner et al. | 514/649 |
| 4,153,722 | 5/1979 | Campbell et al. | 514/644 |
| 4,197,314 | 4/1980 | Campbell et al. | 514/649 |
| 4,214,003 | 7/1980 | Campbell et al. | 514/644 |
| 4,216,231 | 8/1980 | Tanida | 514/645 |
| 4,224,340 | 9/1980 | Campbell et al. | 514/644 |
| 4,870,002 | 9/1989 | Kiel | 435/2 |

FOREIGN PATENT DOCUMENTS

| | | |
|---|---|---|
| 8700629 | 8/1987 | WIPO. |
| 8805653 | 8/1988 | WIPO. |

OTHER PUBLICATIONS

The Merck Manual, 14th ed. (1982) pp. 1305–1309.
Petkova et al., *Agressologie*, 28, 8, pp. 833–834 (1987).
Hearse, et al., J. Mol. Cell. Cardiol., 20, pp. 213–223 (1988).
Bolli, et al., J. Clin. Invest. 82, pp. 476–485 (Aug. 1988).
Weglickl, et al., "Oxy–Radicals in Molecular Biology and Pathology," pp. 357–364 (Proceedings of an Upjohn–UCLA Symposium held at Park City, Utah, Jan. 1988) Editor: Alan R. Liss, Inc. (NY).
E. Masini, et al., Agents and Actions, vol. 27½, pp. 154–157 (1989).
Novelli, et al., "Free Radicals in Liver Injury", pp. 225–228 (IRL Press, Oxford, England, 1985).
Novelli, et al., "Oxygen Free Radicals in Shock", Int. Workshop, Florence 1985, pp. 119–124 (Karger, Basel 1986).
Hearse, et al., "Circulation Research", vol. 60, No. 3, pp. 375–383 (Mar. 1987).
Yanev, et al., "Oxygen Free Radicals in Shock", Int. Workshop Florence 1985, pp. 193–196 (Karger, Basel 1986).
Ilieva, et al., Neurosciences, vol. 12, pp. 223–227 (1986).
Chin et al., Transplantation Proceedings, vol. XIX, No. 1, (1987) pp. 1077–1079.
Hall et al., J. of Neurotrauma, vol. 6, 3, pp. 169–176 (1989).
Hall, E. D., Critical Care Clinics, vol. 5, No. 4, pp. 793–805 (Oct. 1989).
Hamburger et al., Circulatory Shock 29, pp. 329–334 (1989).
McKechnie et al., Circulatory Shock 19, pp. 429–439 (1986).
McCord, J. M. New Eng. J. of Med., vol. 312, No. 3 pp. 159–163 (1985).
Chandler et al., J. of Pharm. Methods, 14, pp. 137–146 (1985).
Baethmann et al., Critical Care Medicine, vol. 16, No. 10, pp. 972–977 (1988).
Hossman, K. A., Critical Care Medicine, vol. 16, No. 10, pp. 964–971 (1988).
Ernster, L., Critical Care Medicine, vol. 16, No. 10, pp. 947–953 (1988).
Siesjo, B. K., Critical Care Medicine, vol. 16, No. 10, pp. 954–963 (1988).
Oliver, et al., Proc. Natl. Acad. Sci. USA, 87, pp. 5144–5147 (1990).
Novelli, G. P. et al., Free Radical Res. Comm., 1 (5) pp. 321–327 (1986).
Novelli, G. P. et al., Free Radical Biol. Med., 8, pp. 9–13 (1990).
Sridhar et al., Oxy. Rad. Chem. Biol., Proc. 3d. Int. Conf. Jul. 10–15, 1983 (publ. 1984) pp. 309–315.
Hearse et al. J. Cardiovasc. Pharmacol., 641–650 (1987).
Bancroft et al., J. Phys. Chem. 84(5), 557–558 (1980).
Phillis et al., Neurosci. Letters, 116, pp. 315–319 (1990).
Dultseva et al., Isv. Sib. Oto. Akad. Nauk (SSSR), Ser Klin Nauk, 1, 77–81 (1989).
Lai et al., Arch. Biochem. Biophys. 244, 156–160 (1986).
Royston, D., Anaesthesia, 43, 315–320 (1988).
Plummer et al., Anesthesiology, 57(3), 160–166 (1982).
Janzen et al., Free Rad. Res. Comms 9(3–6) 325–335 (1990).

(List continued on next page.)

*Primary Examiner*—Raymond Henley, III

[57] ABSTRACT

Compositions containing as the active ingredient a spin-trapping reagent, preferably α-phenyl butyl nitrone (PBN) or spin-trapping derivatives thereof, in a suitable pharmaceutical carrier for administration to a patient are disclosed for treating or preventing symptoms associated with aging or other conditions associated with oxidative tissue damage. Other spin-trapping agents can also be used, such as 5,5-dimethyl pyrroline N-oxide (DMPO) or α-(4-pyridyl 1-oxide)-N-tert-butylnitrone (POBN), and other spin-trapping derivatives thereof. These compositions and methods are useful in the treatment of age-related disorders, pre-surgical and/or pre-anesthetic preparation or administration of chemotherapeutic agents, and in the treatment of disorders or trauma of the brain, cardiovascular system, and lymphatic system. Studies in animals demonstrate that administration of compound for a two week period reduces the level of oxidized brain enzymes to normal and restores memory to the same level as tested in young control animals.

25 Claims, 5 Drawing Sheets

OTHER PUBLICATIONS

Smith et al., Gastroenterology, 92, 950–956 (1987).
Chen et al., Free Rad. Res. Comms. 9(3–6) 317–323 (1990).
Bolli et al., Free Rad. Res. Comms. 9(3–6) 169–180 (1990).
Rau et al., Free Rad. Res. Comms, 9(3–6) 197–204 (1990).
Reinke et al., Free Rad. Res. Comms, 9(3–6) 205–211 (1990).
Janzen et al. Free Rad. Res. Comms. 9(3–6) 353–360 (1990).

Carney et al., J. Mol. Neurosci (1990) 3:47–57.

Floyd et al., Arch. Geront. Geriatr., 12 (1991) 155–177.

Carney et al., Proc. Natl. Acad. Sci. USA, vol. 88, pp. 3633–3636 1991.

Oliver et al., Proc. Natl. Acad. Sci. USA, vol. 87, pp. 5144–5147, 1990.

Kindy et al., J. Mol. Neurosci, 2:217–228 (1991).

Administered to old gerbils (10 mg PBN/kg b.i.d.)

Administered to old gerbils (10 mg PBN/kg b.i.d.)

Administered to old gerbils (10 mg PBN/kg b.i.d.)

METHOD AND COMPOSITIONS FOR TREATING AGE RELATED DISORDERS

This is a divisional of application Ser. No. 08/027,559 filed on Mar. 5, 1993, now U.S. Pat. No. 5,405,874, which is a CONT of Ser. No. 07/589,177, filed Sep. 27, 1990 now abandoned, which is a CIP of Ser. No. 07/422,651, filed Oct. 17, 1989, now U.S. Pat. No. 5,025,032.

BACKGROUND OF THE INVENTION

The present invention is a method and compositions containing spin trapping agents for the treatment of age related dysfunctions and other conditions arising from oxidative damage.

Age related changes in central nervous system function have generally been associated with the loss of cells, a widening of lateral ventricles and deficits in short term memory. The precise mechanisms of functional changes as a result of aging, or other diseases associated with aging, have not generally been agreed upon.

Several mechanisms for the generation of oxidized material in the brain have been proposed. In particular, transition metals, especially iron and copper, have been suggested as mediating aspects of this oxidation. A marked reduction in certain neurotransmitter receptor systems has been associated with increased oxidation of proteins. For example, decreases in muscarinic receptors and other cholinergic systems have been characterized as they relate to alterations in functions in Alzheimers disease. It has also been hypothesized that aging is associated with multiple minor periods of ischemia (multi-infarct conditions or transient ischemia attacks) which, over a period of time, may give rise to the production of oxidized protein.

Changes associated with ischemic brain disease have been proposed to be the result of alterations in calcium disposition, increase in excitoxic neurotransmitter release, production of free radicals and the attendant acidosis that results in an increase in the loosely related metals in the cell that are catalytic for the generation of oxygen free radicals. These changes are largely limited to neuronal elements. Reactive glia have been demonstrated, however, they are mostly associated with postneuronal damage.

The treatment of age related dementias have been largely limited by the inability to develop an appropriate model for the study of this condition. This is due to the fact that aging is a very complicated condition which is difficult to model, especially with the lack of specific information associated with the functional and biochemical basis of human age related dementias. The use of animal models has largely depended upon model systems used in brain studies, where the brains are not truly senescent, or the use of senescent animals, with little understanding of the origin of the senescence or, in some cases, the inability to demonstrate truly functional senescence.

The demonstration in a variety of systems, both neural and nonneural, that there is an age related enhancement of the level of oxidized protein in tissue gives rise to the possibility that age related dysfunctions in the central nervous system may be associated with the build-up of oxidized proteins and oxidized macromolecules within neurons throughout the central nervous system. The hypothesis is that cells which have a buildup of oxidized protein are less functional and less able to maintain the specified role of those cells in that particular area of the central nervous system. While this hypothesis has been suggested by several investigators, there are no reports of substantial investigations in which alterations in the oxidized protein burden of the central nervous system was manipulated and correlated with a functional outcome on the part of the animal. Such an approach, if truly associated with brain dysfunction, would provide a basis for reversing the age related neuronal deficit of cells that are still viable. Thus, such an approach is targeted at cells which are marginally functional but still viable.

It is therefore the object of the present invention to provide composition and methods for the use in preventing or reversing age related functional deficits.

It is further the object of the present invention to provide composition and methods for use thereof which are useful in preventing and reversing cognitive deficits associated with infection or inflammation.

It is another object of the present invention to provide composition and methods reducing post traumatic cognitive dysfunction.

SUMMARY OF THE INVENTION

Compositions containing as the active ingredient a spin-trapping reagent, preferably α-phenyl butyl nitrone (PBN), or spin-trapping derivatives thereof, in a suitable pharmaceutical carrier for patient, are disclosed for treating or preventing symptoms associated with aging or other conditions associated with oxidative tissue damage. The preferred PBN compositions have the following general formula:

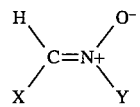

wherein:

X is phenyl or

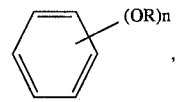

wherein R is H,

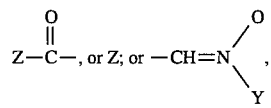

and n is a whole integer from 1 to 5; or

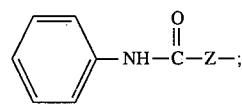

Y is a tert-butyl group that can be hydroxylated or acetylated on one or more positions; phenyl; or

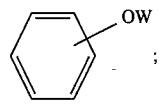

wherein W is

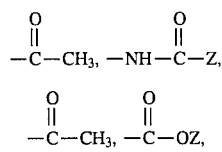

or Z; and

Z is a $C_1$ to $C_5$ straight or branched alkyl group.

Other spin-trapping agents can also be used, such as 5,5-dimethyl pyrroline N-oxide (DMPO) or α-(4-pyridyl 1-oxide)-N-tert-butylnitrone (POBN), and other spin-trapping derivatives thereof.

In the preferred embodiment, the compositions are administered one to two times daily by oral administration, at a dosage equivalent to between one and ten milligrams PBN/ 70 kg of human body weight. Studies in animals demonstrate that administration of compound for a two week period reduces the level of oxidized brain enzymes to normal and restores memory to the same level as tested in young control animals. A significant reduction in oxidized proteins and memory recovery is observed as early as seven days after initiation of treatment; levels are still comparable to young controls one to three days following cessation of treatment, and partially reduced at seven days following cessation of treatment.

These compositions and methods are useful in the treatment of age-related disorders, pre-surgical and/or pre-anesthetic preparation or administration of chemotherapeutic agents, and in treatment of disorders or trauma of the brain, cardiovascular system, lymphatic system, and, potentially, in the treatment of some viral disorders characterized by oxidation of host proteins in cells infected by the virus.

BRIEF DESCRIPTION OF THE FIGURES

FIG. 3A represents the level of carbonyl in the soluble protein obtained from gerbils treated for fourteen days and tested at 1, 3, 7 and 14 days post dosing. FIG. 3B is the time related decrease in cortical glutamine synthetase (GS) activity after termination of twice daily injections of PBN. FIG. 3C demonstrates the time related decrease in alkaline protease activity following termination of twice daily injections of PBN. Each histogram is the mean ± standard error (S.E.) of three subjects at each of the indicated times. The asterisk and dashed line indicates the old gerbil, untreated control values for each of the measures.

FIG. 4A represents the level of carbonyl in the soluble protein obtained from gerbils treated for fourteen days and tested at 1, 3, 7 and 14 days post dosing. FIG. 4B is the time related decrease in cortical glutamine synthetase (GS) activity after termination of twice daily injections of PBN. FIG. 4C demonstrates the time related decrease in alkaline protease activity following termination of twice daily injections of PBN. Each histogram is the mean ± S.E. of three subjects at each of the indicated times. The asterisk and dashed line indicates the old gerbil, untreated control values for each of the measures.

DETAILED DESCRIPTION OF THE INVENTION

Figure 1:
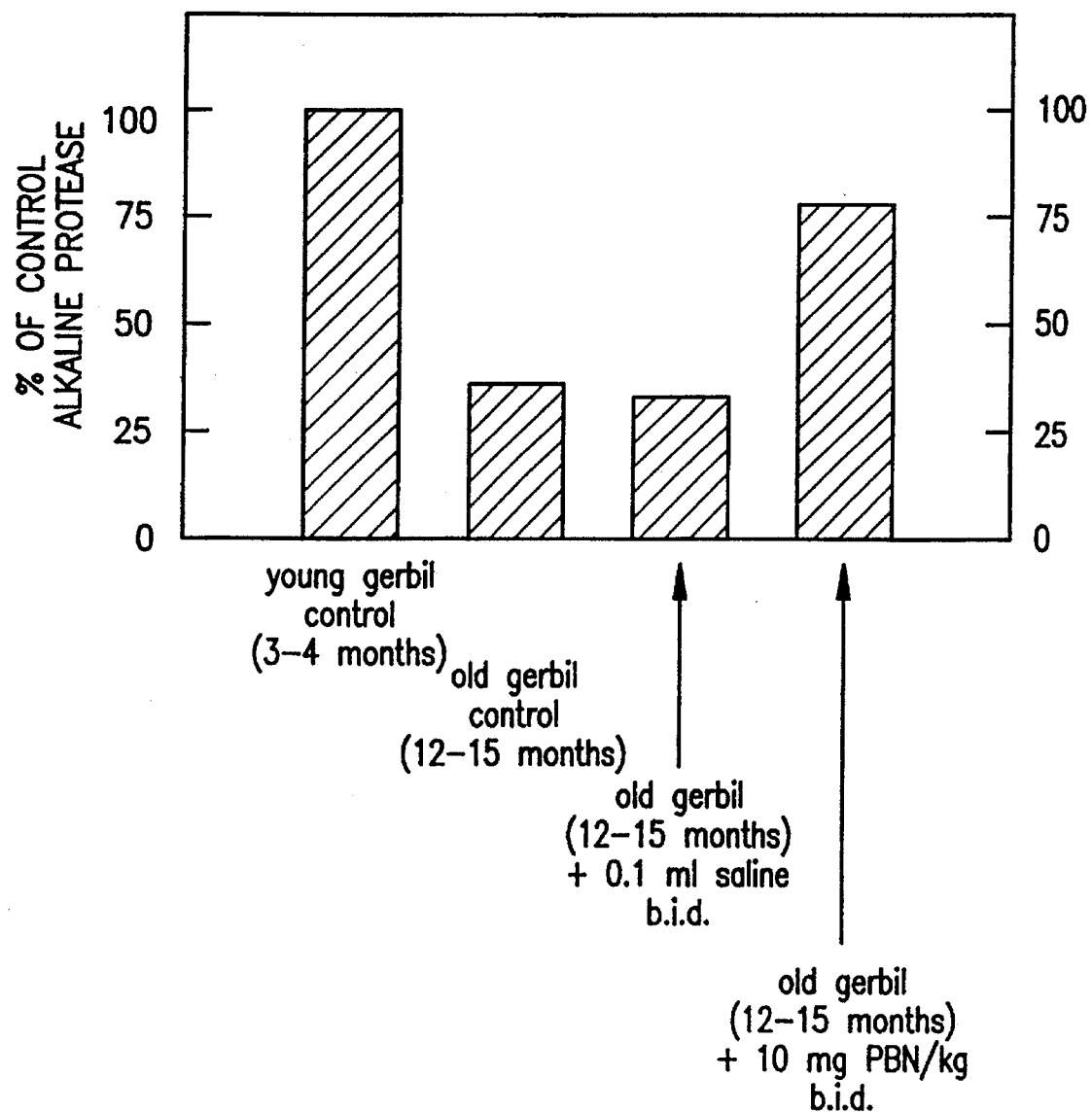
FIG. 1 is a graph of the alkaline protease activity from gerbil cortex (% of young, three to four month old gerbil cortex) for young gerbils (age three to four months), old gerbils (retired breeders of twelve to fifteen months of age), old gerbils that received twice daily injections of 0.1 ml saline/kg body weight, and old gerbils that received twice daily injections of 10 mg PBN in saline/kg body weight for two weeks. Protease activity was determined using oxidized protein extracted from young gerbil cerebral cortex.

It has now been discovered that, further to the methods using PBN for the treatment and prevention of ischemic damage described and claimed in U.S. Ser. No. 07/422,651 filed Oct. 17, 1989, spin-trapping agents are useful in preventing or treating symptoms associated with aging, trauma, drug administration and surgery, especially of the brain. As used herein, a free radical scavenger or spin-trap reagent is a molecule that will form a stable complex with free radical. A free radical carbon trap is a molecule in which the free radical is localized on a carbon atom or a nitrogen atom. As a result of this chemical bond formation, the free radical is no longer damaging to the cell. In combination with a pharmaceutical vehicle suitable for administration to a patient, preferably by oral administration, these compounds are useful in preventing or reversing symptoms associated with aging, for example, increased levels of oxidized proteins, decreased enzymatic activity, and spatial and short term memory. Currently, there are no effective, non-toxic treatments for aging. Effectiveness has been demonstrated in animals after as few as seven days of administration. Effectiveness continues for at least one week after administration. Values return to pre-treatment levels after two weeks.

Useful Spin-trapping Compounds

PBN and Derivatives thereof

The preferred spin-trapping compounds are α-phenyl t-butyl nitrone (PBN), and derivatives thereof. PBN has no measurable effect on normal or uninjured cells. PBN is the preferred compound at this time, although a number of derivatives are also useful, including hydroxy derivatives, especially 2-, 3- or 4-hydroxy PBN and mono-, di- and trihydroxy tert-butyl nitrone; esters, especially esters which release 2-, 3, or 4-hydroxyphenyl t-butyl nitrone such as the acetoxy derivative, 2-, 3-, or 4-carboxyphenyl t-butyl nitrone, such as the ethyl derivative, or phenyl hydroxybutyl nitrone, such as the acetoxy derivative; alkoxyl derivatives, especially alkoxyl derivatives which release 2-, or 4-hydroxyphenyl t-butyl nitrone, such as the methyl derivative; and acetamide derivatives, especially acetamide derivatives which release 2-, or 4 aminophenyl t-butyl nitrone, such as the acetyl derivative; diphenyl nitrone (PPN) and the analogous diphenyl nitrone derivatives. As used herein, "PBN" refers to both phenyl t-butyl nitrone and derivatives thereof, unless otherwise stated.

The general formula for PBN and useful derivatives thereof is:

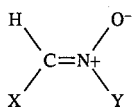

wherein:

X is phenyl or

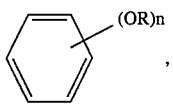

wherein R is H,

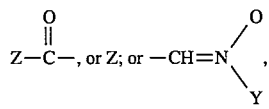

and n is a whole integer from 1 to 5; or

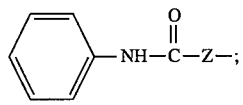

Y is a tert-butyl group that can be hydroxylated or acetylated on one or more positions; phenyl; or

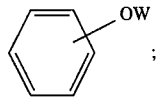

wherein W is

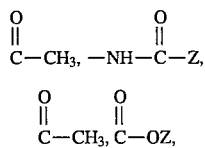

or Z; and

Z is a $C_1$ $C_5$ straight or branched alkyl group.

Other Spin-trapping Reagents

Other spin-trapping agents can also be used, such as 5,5-dimethyl pyrroline N-oxide (DMPO) or α-(4-pyridyl 1-oxide)-N-tert-butylnitrone (POBN), and spin-trapping derivatives thereof. Derivatives are made using standard techniques, for example, for substitution of the methyl groups. The general formula for DMPO is:

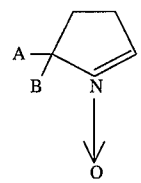

wherein A and B are independendy $CH_3$, $CH_2OH$, $CH_2OW$, or

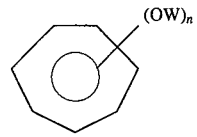

n is an integer from 1 to 5
wherein W is

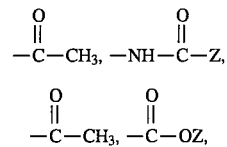

or Z; and

Z is a $C_1$ to $C_5$ straight or branched alkyl group.

The general formula for POBN is:

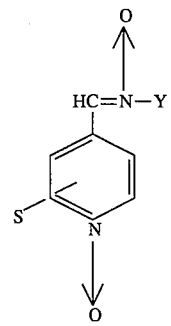

wherein

Y is a tert-butyl group that can be hydroxylated or acetylated on one or more positions; phenyl; or

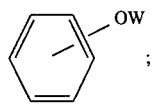

wherein W is

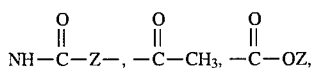

or Z; and

S is H, (OR)$_n$, wherein R is H,

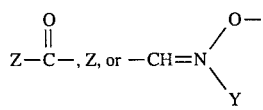

wherein Y is as defined above, n is a whole number from 1 to 4, or

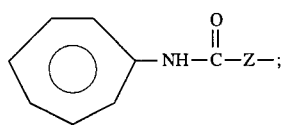

Z is a $C_1$ to $C_5$ straight or branched alkyl group.

Indications that the Compositions are Useful in Treating

The free-radical scavenger compositions are useful in treating a variety of dysfunctions or disorders characterized by oxidized proteins in the tissues or cells. Oxidation of cytosolic protein has been demonstrated to occur in a wide variety of pathological conditions. Accordingly, compounds which have as their fundamental mechanism of action the interference of production of oxidized protein should be useful in the treatment of a wide variety of diseases having what appears at first glance to be widely dissimilar etiologies, because the fundamental cause of the condition is oxidation of protein or nucleic acids.

In one embodiment, the spin-trapping agent is administered to a patient to reverse the damage occurring as a function of age. Preliminary results indicate that there is a net increase in the oxidation of proteins and the accumulation of oxidized material in the brain. The development of senil plaque is also routinely observed in aged patients.

Other disorders are those resulting from trauma, such as a blow to the head, or from drug treatment, for example, administration of anesthesia or drug abuse, or even as a result of some types of viral infections.

It has now been determined that the level of oxidized brain protein appears to be inversely related to performance in a short term memory task and directly related to risk of stroke-induced damage and behavioral change. Increased cellular oxidation may result in one or more of the following: (a) oxidative damage to cellular proteins could cause a change in the regulation of ion channels, there could be a change in the rate and efficiency of signal translation and membrane depolarization, significant changes in energy fluxes may occur and compromise selective function, the fidelity of RNA transcription may be altered due to oxidative damage to DNA, RNA translation may be affected either by oxidation of the RNA or regulatory macromolecules, or the rate of protein degradation may be altered.

Any of these changes could negatively impact on the acquisition consolidation and retrieval of information, even by interference with a single step in the learning and memory process. It is possible that oxidation of cells in a particular brain region could result in acquisition deficits, whereas oxidation of a different region could result in output deficiency. Considering the number of devastating neurodegenerative diseases, including Alzheimer's disease, this treatment could potentially be a tremendous help to people with these disorders.

Examples of other disorders that can be treated with these compositions include peripheral neuropathy of diabetes, exercise induced muscle damage and pain, and enhancement of cellular response to hormonal signals.

Treatment of Neurodegenerative Disorders

Several neurodegenerative conditions are most appropriately treated by compounds that interfere with protein oxidation. Alzheimer's disease has been associated with the accumulation of abnormal oxidized proteins or the production of abnormal proteins in areas that are pathologically affected. In addition, age related enhancement in protein oxidation occurs in all cells in the aged individual. PBN and derivatives thereof have been demonstrated to be useful in the reduction in protein oxidation and in the increase in the activity of critical enzymes within the brain of aged animals. Since this is a fundamental change in oxidative state, it is likely that PBN and other related compounds would be useful when given chronically to individuals who are in the early phases, or possibly in the late phases, of Alzheimer's disease. In addition, multi-infarct dementias should be treatable with these compounds, since they also deal with ischemia reperfusion oxidation issues.

Senile dementia has not been directly evaluated for ischemia reperfusion etiology or protein oxidation, however, it is likely that senile dementia would also be treatable with these compounds. This is based on the hypothesis that advanced age is associated with increased production of oxidized protein. In progeria, a unique condition in which aging is accelerated, Stadtman and colleagues at the NIH have demonstrated that there is a marked increase in the base-level of oxidized protein even in young adult subjects with progeria, as reported by Oliver, et al., *J. Biol. Chem.* 262, 5488–5491 (1987) and Starke-Reed and Oliver, *Arch. Biochem. Biophys.* 275, 559–567 (1989). While this is a rare condition it should also be treatable with these compositions.

Another condition which is likely to be associated with oxidative damage arising from microcirculatory difficulties is the diabetic peripheral neuropathies and vascular change. These are tragic conditions in which amputation is eventually necessary in order to save the patient. While these compounds are not likely to improve vascular flow they are likely to reduce the impact of transient changes in vascular flow which result in oxidation and damage to the peripheral nerves and also in damage to the skeletal muscle which is often associated with the condition called exercise induced or intermittent claudication. If the retinopathy associated with diabetes is also an ischemia reperfusion microcirculation problem, then the spin-trapping compounds will be useful in treating the retinal damage which occurs very frequently in diabetic patients.

Pre-surgical Preparation

Since the status of the cell and its survival in a hypoxic or anoxic environment is dependent upon the ability of the cell to compartmentalize metals and handle oxygen in a useful manner, in contrast to peroxidation, it is expected that these compounds will be useful as presurgical preparatory medication to reduce the carbonyl load and improve the enzyme status of the patient prior to elective surgery. These compounds would also help the cells of the body achieve a higher level of enzymatic function, shorten the recuperative phase, and reduce the likelihood of any interoperative complications associated with changes in microcirculation.

Treatment of Viral Infections and Inflammatory Disorders

Retroviruses selectively infect certain types of cells, such as lymphocytes. An example of a retrovirus that has been the subject of much research activity is the human immunodeficiency virus (HIV), which causes Acquired Immunodeficiency Syndrome (AIDS). No means for prevention of infection has been found, although there have been numerous attempts to find a treatment. Since activation of lymphocytes is associated with the oxidation of protein and activation of lymphocytes is required prior to release of newly formed viruses, it is expected that administration of these compositions will inhibit infection and replication of lymphocytes by the viruses. The activation of the T-4 lymphocyte is associated with a cascade of biochemical intracellular changes, one of which is the production of oxidized protein. If PBN related compounds can block protein oxidation in the abnormal process then it is possible that PBN or other spin-trappin compounds could in fact interfere with the process of viral replication and/or dissemination of the virus from the host cell (T-4 lymphocyte), thereby acting as a virustatic agent by preventing the T-4 lymphocyte from releasing the newly formed viruses. This would be analogous to the use of isoniazid (INH) in the treatment of tuberculosis. At low doses INH is a tubercula static in that it reduced the infectivity and spread of the tuberculosis, thereby effectively protecting the patient from pulmonary damage.

It is important to note that the effects of the spin-trapping compounds occur in animals that have a base-level of carbonyl formation which appears to be necessary for post translational processes. Old animals have a significantly elevated level of carbonyl protein which is associated with decreased enzymatic function relative to young control animals. When young control animals are given the exact same dosage regimen, there is no significant change in enzyme activity nor is there significant change in protein carbonyl. Thus the PBN and related spin-trapping compounds are not likely to interfere with fundamental processes that are necessary for the normal cellular function.

In conclusion, a number of clinical conditions appear to have as their fundamental cause oxidation of cellular protein and enzymatic damage. Spin-trapping compounds are effective in animal models in reducing the protein oxidation and improving enzymatic function. This occurs in preparations in which the abnormal oxidized protein is modified and protected but the normal post translational oxidation is allowed to occur. This would suggest that PBN does not interfere with the normal necessary oxidation of proteins following synthesis.

Effective Dosages of PBN

Exemplary dosages of PBN range from 0.1 to 10 mg/kg of body weight in animals. The effectivedosage of PBN in humans is expected to be between approximately 1 and 10 mg/70 kg body weight. Toxicity tests have demonstrated that the compound is completely innocuous, with such low toxicity that it was not possible to determine an $LD_{50}$.

In the preferred application, the PBN is administered to a patient suffering from memory loss or other symptoms frequently associated with aging. Optimum results are generally observed after two weeks of daily or twice daily oral administration. The compositions can also be effectively administered prior to, during or shortly after surgery, and prevent or decrease the extent of cellular damage resulting from either the trauma or anesthesia.

Since the trapping of endogenous free radicals is specific for only those cells that have been exposed to the conditions that result in the production of free radicals, the traps have little or no effect on normal cells. The beneficial effects occur only in injured cells, and do not require the presence of specific receptors, specific enzymes, and/or specific cell types.

Methods of Administration of PBN

The PBN is preferably administered systemically, most preferably orally, since this is the most rapid and efficient means for delivering the active compound to the site of free radical generation. The PBN may be administered at once, or may be divided into a number of smaller doses to be administered at varying intervals of time. Other methods of administration can also be used, including subcutaneous, intravenous, and intraperitoneal administration. The concentration of active compound in the drug composition will depend on absorption, inactivation, and excretion rates of the drug as well as other factors known to those skilled in the art. The effective dosage may also be determined based on that amount required to prevent or reverse predisposition of the cells to damage resulting from depletion of ATP (as demonstrated by in vivo NMR) and damage from free radical generation. It is to be noted that dosage values will also vary with the condition of the patient being treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

A preferred mode of administration of the active compound is in a form for oral delivery. Oral compositions will generally include an inert diluent or an edible carrier. Preferred pharmaceutical carriers for intravenous administration are saline or phosphate buffered saline at physiological pH. Since PBN degrades at pH less than approximately 3 to 4, it is preferred to administer the PBN at a pH of 4 or higher, or in combination with food, a buffering agent, or in an enteric coating. For oral delivery, the PBN may be enclosed in capsules, compressed into tablets, microencapsulated, entrapped in liposomes, in solution or suspension, alone or in combination with a substrate immobilizing material such as starch or poorly absorbable salts such as immodium. Pharmaceutically compatible binding agents can be included as part of the composition. The tablets or capsules may contain, for example, any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier. In addition, dosage unit forms can contain various other materials which modify the physical form of the dosage unit, for example, coatings of sugar, shellac, or other enteric agents.

The present invention will be further understood with reference to the following non-limiting examples demonstrating methods for determining effectiveness of PBN administration for treatment or prevention and/or reversal of symptoms associated with aging.

EXAMPLE 1

Determination of Brain Enzyme Levels in Old Versus Young Gerbils Treated with PBN A correlations between the duration of ischemia and either the change in spontaneous behavior or the level of oxidized brain protein has previously been demonstrated in gerbils. Many other psychiatric and neurological conditions have been proposed to be the result of oxidation, Among these conditions, cellular aging has been associated with oxygen radicals and the accumulation of proteins. The level of oxidized protein, glutamine synthetase activity, brain protease activity and radial arm maze performance in young adult and retired breeder gerbils have now been compared and demonstrate that there is a direct relationship between the age of the subject and the level of oxidized brain protein, as measured using a protein carbonyl assay. Increased levels of protein carbonyl were associated with decreased glutamine synthetase activity and decreased alkaline protease activity. In contrast, there was no change in acid protease activity of retired breeders, compared to young adult gerbils. Consistent with the age-related increase in protein oxidation and enzyme damage, retired gerbils made significantly greater numbers of errors in a test of short-term memory, compared to young adult gerbils. These studies demonstrate that the functional deficits that occur as a result of aging may be associated with increased protein oxidation and decreased brain enzyme activities.

This system has been used to demonstrate the effectiveness of PBN in restoring young brain enzyme levels and short term memory to old animals. The results are shown in FIGS. 1 through 5, as follows. Young gerbils were obtained from Tumblebrook Farms, West Brookfield, Mass., weighing 50–60 grams and age three to four months. Control gerbils were given saline. Animals were killed by decapitation and their brains removed for analysis.

FIG. 1A is a graph of the percent alkaline protease in young (three to four month old) gerbils, old (twelve to fifteen month old retired breeder) gerbils, old gerbils administered 0.1 ml saline twice daily (b.i.d.), and old gerbils administered 10 mg PBN/kg body weight b.i.d. for fourteen days.

The results demonstrate that PBN is effective in restoring alkaline protease levels in old animals to those levels present in young animals.

Figure 2A:
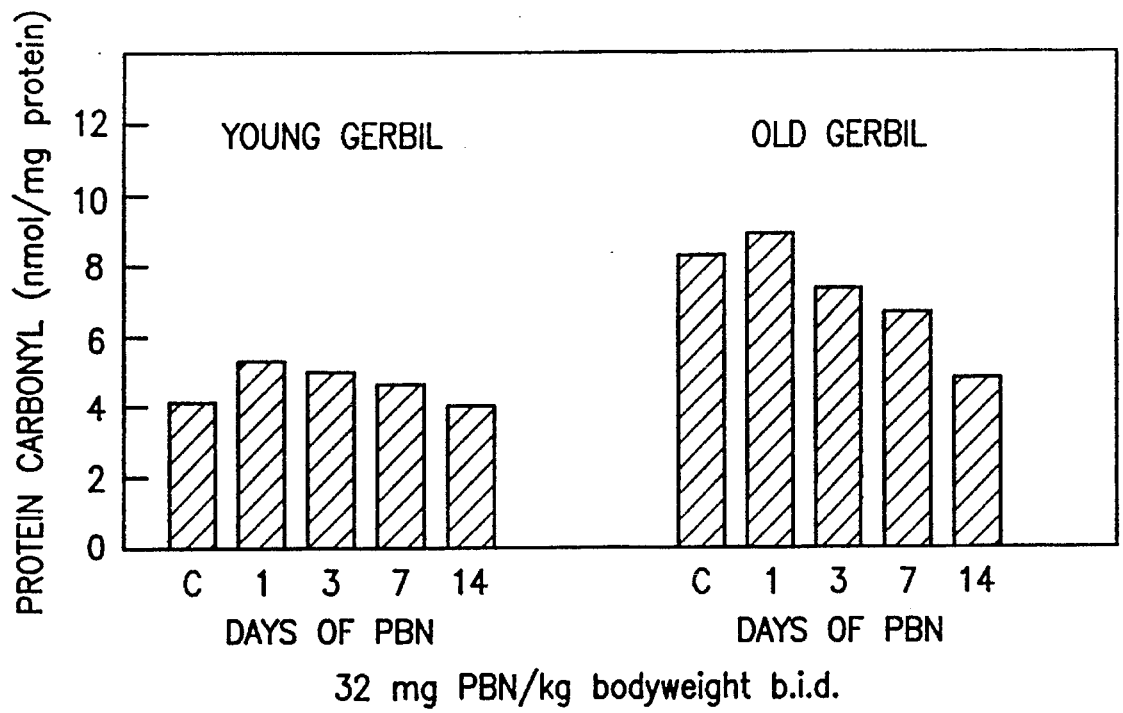
FIG. 2A and FIG. 2B are graphs comparing protein carbonyl activity (pmol/mg protein) (FIG. 2A) and glutamine synthetase activity (FIG. 2B) in the cerebral cortex (neocortex) of young adult and old gerbils over days of administration of 32 mg PBN/kg administered twice a day for one, three, seven or fourteen days. At the end of each of the days indicated, animals were decapitated and cerebral cortex removed and rapidly frozen in liquid nitrogen. Protein carbonyl content was determined using the DNPH procedure. The results demonstrate the reduction in oxidative damage to proteins and the loss of enzyme activity in gerbil cerebral cortex as a result of twice daily administration of 32 mg PBN/kg (i.p.). Each histogram is the mean of three subjects.

FIG. 2A is a graph of the changes in protein oxidation from brains of young and senescent gerbils, plotting nmol protein carbonyl/mg protein versus days of treatment with PBN. The gerbils were given twice daily injections of 32 mg/kg PBN for fourteen days. Animals were killed at one, three, seven and fourteen days and protein carbonyl levels determined.

As can be seen in the figure, there is no change in the level of oxidized protein of young gerbils treated for up to 14 days with PBN. This indicates that the level of oxidized protein is likely to be a natural and necessary post translational effect, for example, if after synthesis of the protein, the protein is activated by a modification involving carbonyl oxidation. In contrast to the carbonyl level seen in young animals, control aged animals (15 months of age) have a marked increase of carbonyl content. This increased carbonyl content is responsive to treatment with PBN. Multiple days of treatment with PBN results in a progressive reduction in the level of protein carbonyl to the level seen in young animals.

The level of protein carbonyl reduction (oxidized protein burden of neurons in the brain) is only to the level of the normal young gerbil brain. Neither the levels in the young gerbil brain nor the levels in the senescent gerbil brain can be further reduced beyond this level. This observation supports the hypothesis that there is a necessary level of oxidation that occurs in cells in normal animals, which is required for cells to have "normal function", and that control aged animals (15 months of age) have a marked increase of carbonyl content. This increased carbonyl content is responsive to treatment with PBN. The ability of PBN to reduce the protein carbonyl load of cells also indicates that this is an active oxidation process which occurs at a regular or predictable rate and that there are mechanisms existent within the cells of the brain which can remove this oxidized protein if the process is interrupted.

Figure 2B:
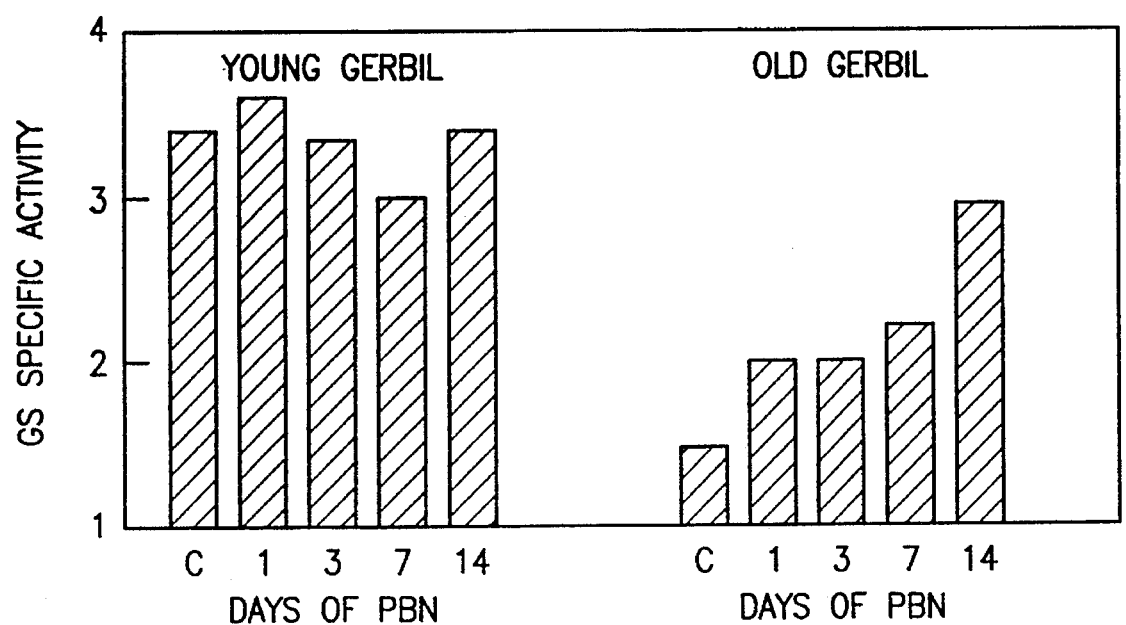

FIG. 2B compares the levels of glutamine synthetase (gs) in young and old animals and evaluates the effects of daily administration of PBN on the specific activity of the enzyme. This particular enzymatic marker has been selected because it is a highly sensitive protein to oxidation and because it is a metalloprotein that has bound to it metal which may participate in the generation of free radicals if the metal is dissociated with its binding site. Glutamine synthetase activity has been used by Stadman and colleagues (Oliver, et al., *Proc. Natl. Acad. Scie. USA* 87, 5144–5147 (July 1990)) as a marker enzyme for alterations following protein oxidation.

As shown in FIG. 2B, the level of glutamine synthetase is lower in old gerbils (1.2) than in young adult gerbils (2.1). This is consistent with previous studies in which increases in the level of the carbonyl protein (oxidized protein in cells) is associated with a decrease in glutamine synthetase activity. In particular, if the glutamine synthetase enzyme is purified and the carbonyl content of that enzyme is evaluated, there is a marked increase in the level of oxidized protein in the presence of lowered glutamine synthetase activity. As also demonstrated in FIG. 2B, repeated administration of PBN in young gerbils had no effect on glutamine synthetase activity, providing further evidence that the level of carbonyl is associated with normal function and chronic administration of PBN has no effect on either the level of carbonyl or on the marker enzyme activity. In contrast to the young gerbils, old gerbils given daily injections of PBN show a time related increase in glutamine synthetase activity that parallels the reduction in protein carbonyl content, indicating that the reduction in oxidized protein burden of cells is associated with a recovery of the enzymatic activity to the normal level seen in young adult gerbils.

It is important to note that there is no increase in enzymatic activity above that seen in young adult gerbils. Thus the treatment with PBN reverses the effect of aging on enzymatic activity but does not result in an activation of enzyme activity that exceeds the normal values.

EXAMPLE 2

Determination of Residual Effect of PBN on Reduction of Brain Enzyme Levels

Figure 3A:
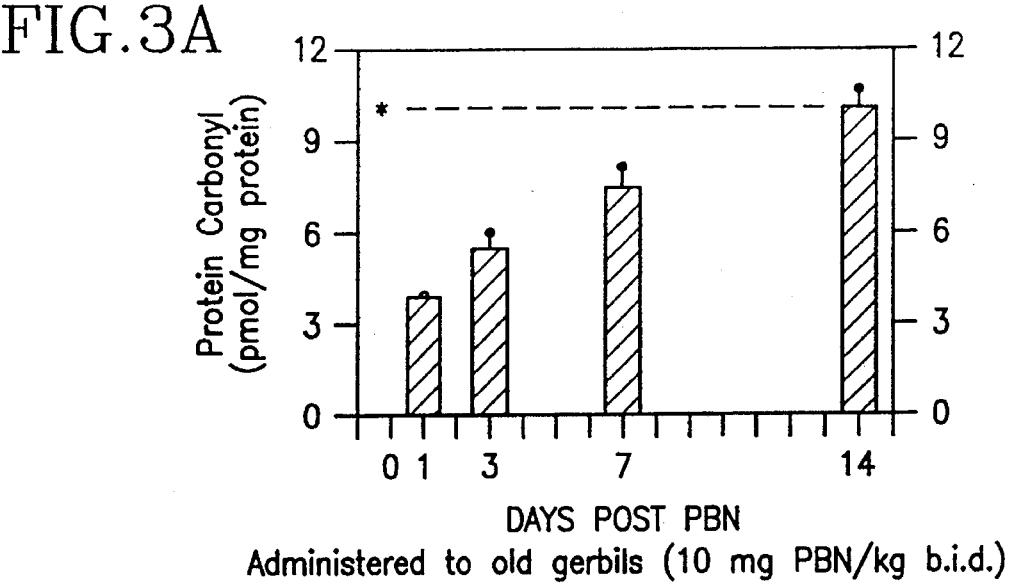
FIGS. 3A, 3B and 3C are graphs comparing changes in protein carbonyl (pnol/mg protein) (FIG. 3A), glutamine synthetase (FIG. 3B), and protease activity (% control) (FIG. 3C) over days following termination of twice daily dosing with 10 mg PBN/kg body weight.
Figure 3B:
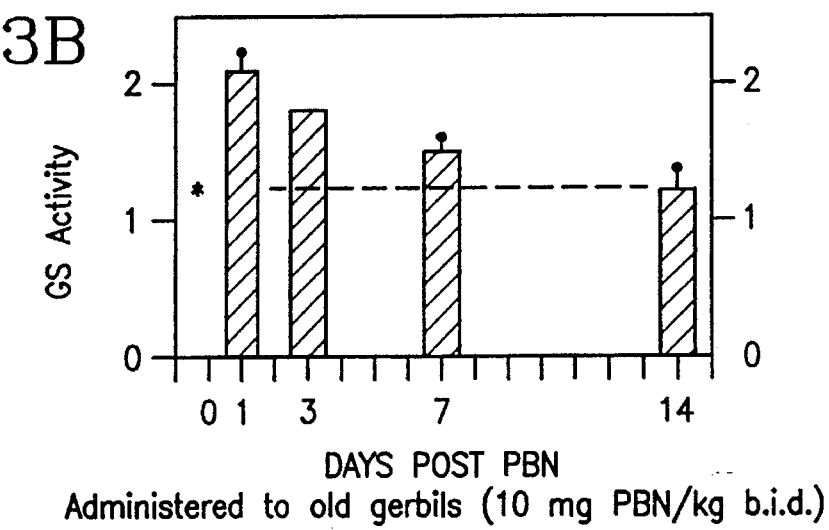
Figure 3C:
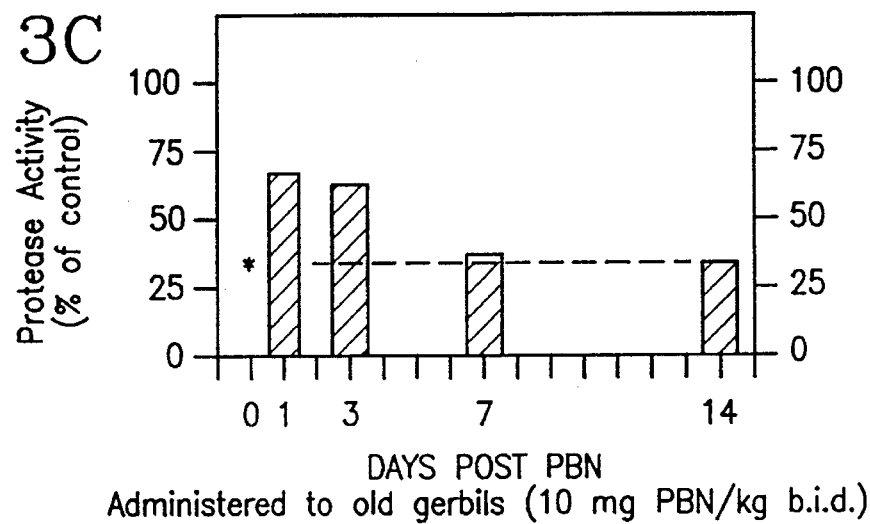
Figure 4A:
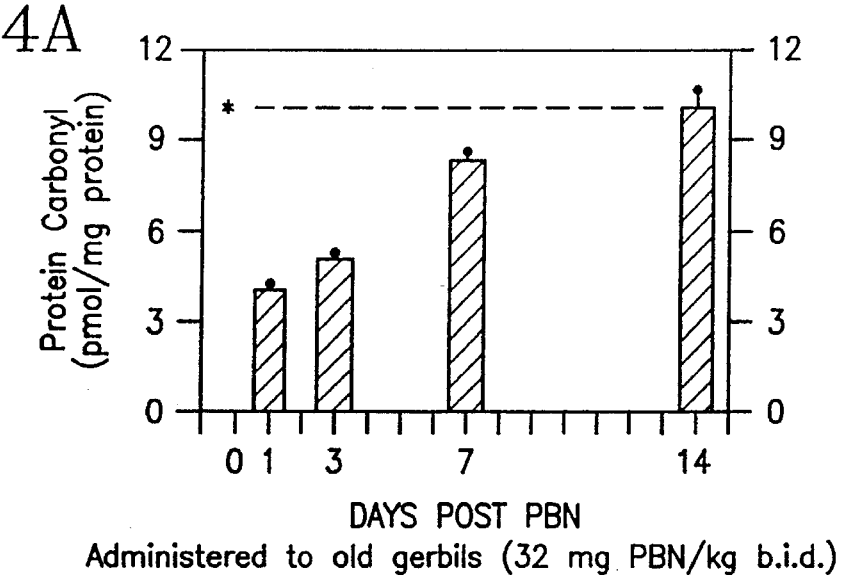
FIGS. 4A, 4B and 4C are graphs comparing changes in protein carbonyl (pnol/mg protein) (FIG. 4A), glutamine synthetase (FIG. 4B), and protease activity (% control) (FIG. 4C) over days following termination of twice daily dosing with 32 mg PBN/kg body weight.
Figure 4B:
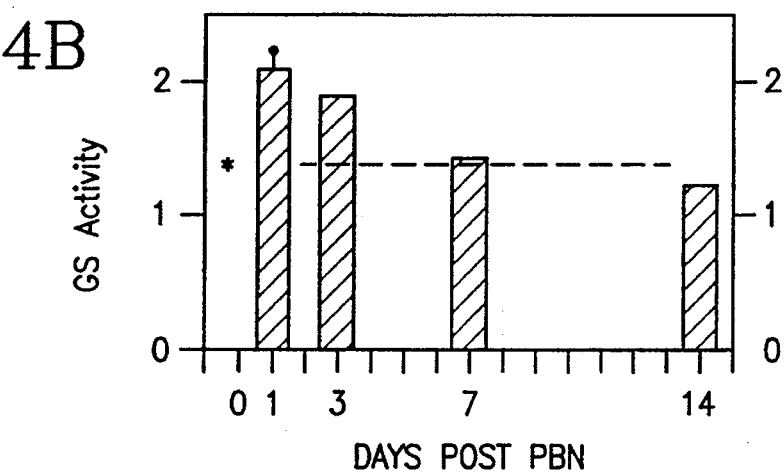
Figure 4C:
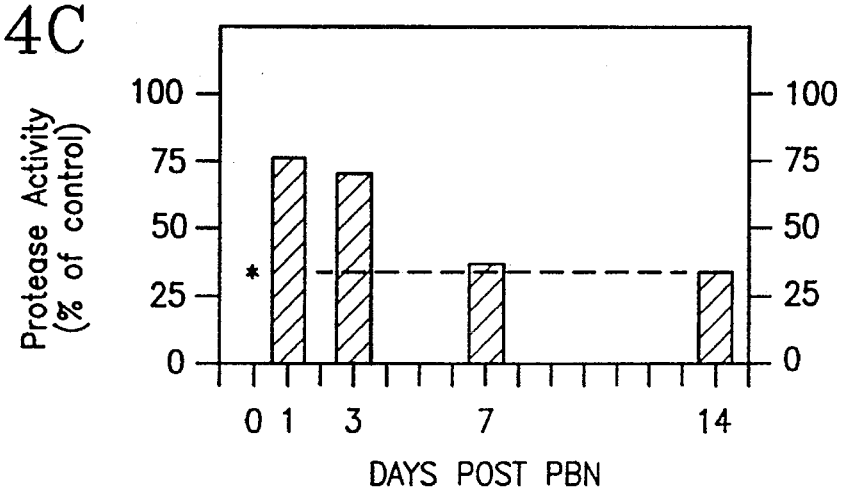

As shown in FIGS. 3A, 3B, and 3C, as compared with FIGS. 4A, 4B, and 4C, administration of 10 mg PBN/kg is as effective as administration of 32 mg PBn/kg body weight in restoring young enzyme levels. The appropriate dosages and full range of effective dosages for other species of animals can be determined using a similar methodology.

The time related changes in protein oxidation and enzyme activity following termination of twice daily dosing with either 10 mg PBN/kg (FIGS. 3A, B, and C) or 32 mg PBN/kg (FIGS. 4A, B, and C) are also shown by these figures. The results demonstrate that the effect of the PBN is unaltered one to three days after termination of treatment twice daily with the PBN, although the PBN itself has a half-life of three hours. At seven days, the enzyme levels are altered by approximately 50%. At fourteen days, the oxidized enzymes have returned to approximately their pretreatment levels.

EXAMPLE 3

Figure 5:
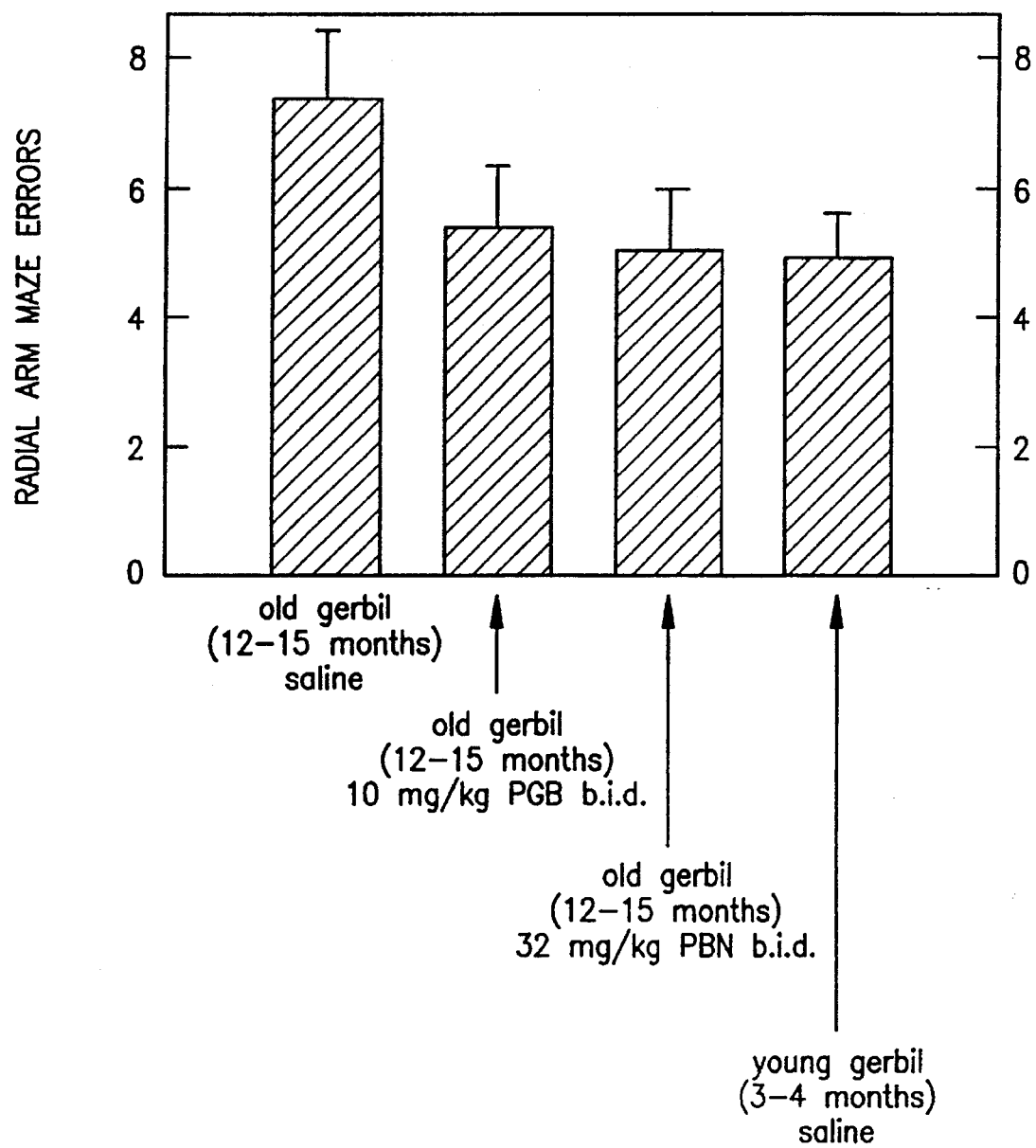
FIG. 5 is a graph of the eight arm radial arm maze performance of young or old gerbils treated with either saline or PBN. Gerbils were placed into the central compartment of the maze with the barrier in place to limit exploration. After the barrier was removed, the number of arms re-entered and the total elapsed time before all eight arms were entered was recorded. Each histogram represents the mean ± of 18 gerbils. The animals were administered PBN twice daily (either 10 or 32 mg PBN/kg body weight) for seven days and tested at the end of seven days of dosing.

Demonstration of Correlation Between Effect of PBN on Brain Enzymes and Memory FIG. 5 demonstrates that there is a functional counterpart to such treatment. Young and old gerbils were tested in a radial arm maze test for spacial and short term memory. Animals were placed in the central hub of a eight armed radial maze and given access to explore all eight arms of the radial arm maze. When the animal completed the test of exploring each of the eight arms, the animal was removed from the maze. The number of times that the animals reentered arms that had been previously entered was counted as an error. Under ideal conditions animals will enter each one of the eight arms but not reenter any of the arms. In many cases young adult gerbils (young) entered each of the arms without reentering any of the arms. The time required to enter all eight arms was also recorded but did not appear to determine the efficiency of the short term memory task. As can be seen in FIG. 5, young gerbils made an average of 2.83 errors during the test session. In contrast, old gerbils made an average of 6.82 errors, which is a highly significant difference between the two groups.

Young adult gerbils exposed to a period of transient ischemia, which is also an oxidizing process, make a substantial number of errors with an average value of 15 errors in such a test session. During the post ischemic period, there is a marked build up of carbonyl protein and reduction in glutamine synthetase activity similar to that which is seen in aging.

Treatment of gerbils for seven days results in a marked alteration in the number of errors seen with old gerbils. Young gerbils given PBN for seven days were not significantly different from control gerbils whereas the old gerbils given PBN for seven days showed a marked reduction in the number of errors and returned to the range of performance seen with control young gerbils. Thus, there is a functional counterpart to the biochemical changes that are seen in that reduction in protein carbonyl and the increase in glutamine synthetase activity following chronic PBN treatment. This functional counterpart is demonstrated by the number of errors seen in a short term spacial memory task, the radial arm maze. It should be noted that the radial arm maze test does not require any food reinforcement or any other reward associated with the test. Naive animals are placed into the radial arm maze, are tested once and these differences are reliable on retest.

Modifications and variations of the method and composition for the treatment of aging will be obvious to those skilled in the art from the foregoing detailed description. Such modifications and variations are intended to come within the scope of the appended claims.

We claim:

1. A method of improving short term memory in a patient suffering from short term memory loss comprising administering to said patient an effective amount of a composition capable of treating said short term memory loss and improving short term memory, said composition having as the active agent a compound selected from the group consisting of 5,5-dimethyl pyrroline N-oxide (DMPO); α-(4-pyridyl 1-oxide)-N-tert-butylnitrone (POBN); and derivatives thereof selected from the group consisting of hydroxy POBNs and DMPOs, POBN and DMPO esters, acetoxy POBNs and DMPOs, alkyl POBNs and DMPOs, alkoxy POBNs and DMPOs and phenyl POBNs and DMPOs having spin trapping activity in vivo in tissue; and a pharmaceutically acceptable carrier therefor.

2. The method of claim 1 wherein the compound is provided in a dosage of between 1 and 300 mg/kg body weight.

3. The method of claim 2 wherein the compound is provided in a dosage of between 1 and 10 mg/kg body weight.

4. The method of claim 1 wherein the active agent is 5,5-dimethyl pyrroline N-oxide.

5. The method of claim 1 wherein the active agent has the formula:

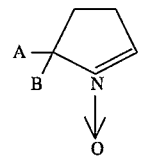

wherein A and B are independently $CH_3$, $CH_2OH$, $CH_2OW$, or

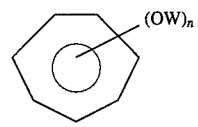

n is an integer from 1 to 5
wherein W is

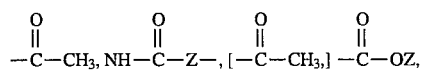

or Z; and

Z is a $C_1$ to $C_5$ straight or branched alkyl group.

6. The method of claim 1 wherein the active agent is α-(4-pyridyl 1-oxide)-N-tert-butylnitrone.

7. The method of claim 1 wherein the active agent has the formula:

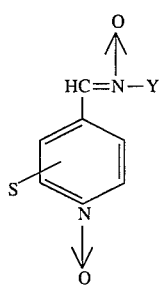

wherein
Y is a tert-butyl group that can be hydroxylated or acetylated on one or more positions; phenyl; or

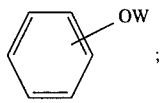

wherein W is

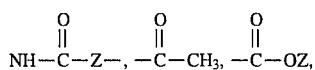

or Z; and
S is H, $(OR)_n$, wherein R is H,

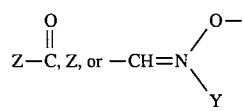

wherein Y is as defined above,
n is a whole number from 1 to 4, or

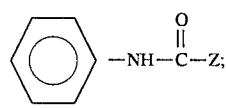

and
Z is a $C_1$ to $C_5$ straight or branched alkyl group.

8. The method of claim 1 wherein the active agent is provided in combination with a pharmaceutical carrier selected from the group consisting of microspheres, liposomes, immobilizing substrates, polymeric matrices and buffering agents.

9. The method of claim 1 wherein the short term memory loss is associated with ischemia.

10. The method of claim 1 wherein the short term memory loss is associated with progressive neuronal loss.

11. The method of claim 1 wherein the progressive neuronal loss is due to Parkinson's disease.

12. The method of claim 1 wherein the progressive neuronal loss is due to senile dementia.

13. The method of claim 1 wherein the progressive neuronal loss is due to Alzheimer's disease.

14. A method for improving short term memory in a patient suffering from short term memory loss comprising administering to said patient an effective amount of a compound selected from the group consisting of:

(a) at least one compound of the formula:

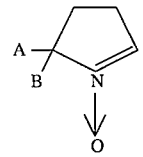

wherein A and B are independently $CH_3$, $CH_2OH$, $CH_2OW$, or

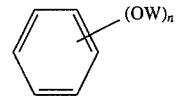

n is an integer from 1 to 5
wherein W is

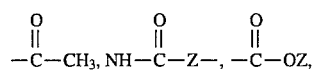

or Z; and
Z is a $C_1$ to $C_5$ straight or branched alkyl group;

(b) at least one compound of the formula

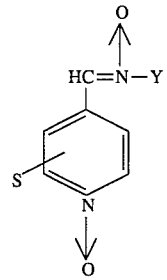

wherein
Y is a tert-butyl group that can be hydroxylated or acetylated on one or more positions; phenyl or

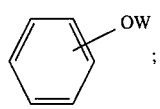

wherein W is

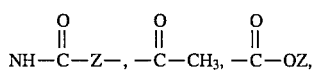

or Z; and
S is H, $(OR)_n$, wherein R is H,

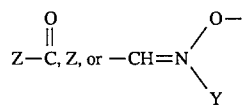

wherein Y is as defined above, n is a whole number from 1 to 4, or

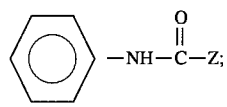

and

Z is a $C_1$ to $C_5$ straight or branched alkyl group;

(c) at least one other 5,5-dimethyl pyrroline N-oxide (DMPO) derivative selected from the group consisting of hydroxy DMPOs, DMPO esters, acetoxy DMPOs, alkyl DMPOs, alkoxy DMPOs and phenyl DMPOs having spin trapping activity in vivo in tissue; and (d) at least one other alpha-(4-pyridyl 1-oxide)-N-tert-butylnitrone (POBN) derivative selected from the group consisting of hydroxy POBNs, POBN esters, acetoxy POBNs, alkyl POBNs, alkoxy POBNs and phenyl POBNs having spin trapping activity in vivo in tissue, optionally in association with a pharmaceutically acceptable carrier.

15. A method according to claim 14 wherein said compound is provided in combination with a pharmaceutical carrier.

16. A method according to claim 14 wherein said compound is provided in combination with a pharmaceutical carrier selected from the group consisting of microspheres, liposomes, immobilizing substrates, polymeric matrices, and buffering agents.

17. A method according to claim 14 wherein said compound is administered in a dosage of from 1 to 300 mg/kg body weight.

18. A method according to claim 14 wherein said compound is administered in a dosage of from 1 to 10 mg/kg body weight.

19. The method of claim 14 wherein the short term memory loss is associated with ischemia.

20. The method of claim 14 wherein the short term memory loss is associated with progressive neuronal loss.

21. The method of claim 20 wherein the progressive neuronal loss is due to Parkinson's disease.

22. The method of claim 20 wherein the progressive neuronal loss is due to senile dementia.

23. The method of claim 20 wherein the progressive neuronal loss is due to Alzheimer's disease.

24. The method of claim 14 wherein Y is tert-butyl.

25. The method according to claim 1 wherein said compound is provided in combination with a pharmaceutical carrier selected from the group consisting of microspheres, liposomes, immobilizing substrates, polymeric matrices, and buffering agents.

* * * * *